(12) United States Patent
Gamache et al.

(10) Patent No.: US 8,425,515 B2
(45) Date of Patent: Apr. 23, 2013

(54) BONE GRAFT LOADING INSTRUMENTS AND METHODS OF CONNECTING A BONE GRAFT TO A BONE PLATE

(75) Inventors: Thomas J Gamache, Westport, MA (US); Michael D Sorrenti, Middleboro, MA (US); Edward Zalenski, Lakeville, MA (US)

(73) Assignee: DePuy Spine, Inc., Raynham, MA (US)

( * ) Notice: Subject to any disclaimer, the term of this patent is extended or adjusted under 35 U.S.C. 154(b) by 479 days.

(21) Appl. No.: 12/609,260

(22) Filed: Oct. 30, 2009

(65) Prior Publication Data

US 2011/0106084 A1    May 5, 2011

(51) Int. Cl.
*A61B 17/56*    (2006.01)
*A61B 17/58*    (2006.01)
*A61B 17/80*    (2006.01)
*A61F 2/30*    (2006.01)

(52) U.S. Cl.
USPC .............................. 606/70; 606/246; 606/279

(58) Field of Classification Search ............... 606/280, 606/281; 206/733, 734, 211, 214, 6.1, 339, 206/343
See application file for complete search history.

(56) References Cited

U.S. PATENT DOCUMENTS

| | | | |
|---|---|---|---|
| 4,972,949 A * | 11/1990 | Peiffer | ........................... 206/339 |
| 5,085,660 A | 2/1992 | Lin | |
| 5,133,735 A | 7/1992 | Slater | |
| 5,133,736 A | 7/1992 | Bales, Jr. | |
| 5,141,519 A | 8/1992 | Smith | |
| 5,147,360 A | 9/1992 | Dubousset | |
| 5,147,378 A | 9/1992 | Markham | |
| 5,152,778 A | 10/1992 | Bales, Jr. | |
| 5,152,780 A | 10/1992 | Honkanen | |
| 5,176,702 A | 1/1993 | Bales | |
| 5,192,298 A | 3/1993 | Smith | |
| 5,199,566 A | 4/1993 | Ortiz | |

(Continued)

FOREIGN PATENT DOCUMENTS

| WO | WO 9511632 | 5/1995 |
|---|---|---|
| WO | WO 9512356 | 5/1995 |

(Continued)

OTHER PUBLICATIONS

Frank, "A Technique for Cervical Laminoplasty Using Mini Plates", British Journal of Neurosurgery, 1994, vol. 8, pp. 197-199.

(Continued)

*Primary Examiner* — Andrew Yang
(74) *Attorney, Agent, or Firm* — David A. Lane, Jr.

(57) ABSTRACT

An instrument for positioning a bone graft relative to a bone plate includes an instrument body having a plurality of spaced apart graft chambers, a first one of the graft chambers having a first end, a second end, and a chamber length extending between the first end and the second end, the first end of the first graft chamber including a first chamber surface for receiving a first plate segment of a first bone plate, the second end of the first graft chamber including a second chamber surface for receiving a second plate segment of the first bone plate, the first graft chamber including a central chamber surface interposed between the first chamber surface and the second chamber surface for receiving a first bone graft, the central chamber surface having a first chamber length corresponding to the graft length of the first bone grafts.

22 Claims, 5 Drawing Sheets

U.S. PATENT DOCUMENTS

| | | | |
|---|---|---|---|
| 5,290,299 A | 3/1994 | Fain |
| 5,336,228 A | 8/1994 | Cholhan |
| 5,366,455 A | 11/1994 | Dove |
| 5,380,324 A | 1/1995 | Muller |
| 5,411,522 A | 5/1995 | Trott |
| 5,423,826 A | 6/1995 | Coates |
| 5,466,243 A | 11/1995 | Schmieding |
| 5,470,333 A | 11/1995 | Ray |
| 5,487,741 A | 1/1996 | Maruyama |
| 5,498,263 A | 3/1996 | DiNello |
| 5,501,683 A | 3/1996 | Trott |
| 5,507,747 A | 4/1996 | Yuan |
| 5,527,312 A | 6/1996 | Ray |
| 5,531,745 A | 7/1996 | Ray |
| 5,558,674 A | 9/1996 | Heggeness |
| 5,616,144 A | 4/1997 | Yapp |
| 5,637,112 A | 6/1997 | Moore |
| 5,704,936 A | 1/1998 | Mazel |
| 5,722,976 A | 3/1998 | Brown |
| 5,735,852 A | 4/1998 | Amrein |
| 5,735,899 A | 4/1998 | Schwartz |
| 5,746,743 A | 5/1998 | Greenberg |
| 5,830,231 A | 11/1998 | Geiges, Jr. |
| 5,922,008 A | 7/1999 | Gimpelson |
| 5,951,557 A | 9/1999 | Luter |
| 5,961,530 A | 10/1999 | Moore |
| 5,993,449 A | 11/1999 | Schlapfer |
| 6,080,157 A | 6/2000 | Cathro |
| 6,136,002 A | 10/2000 | Shih |
| 6,273,253 B1 | 8/2001 | Forster |
| 6,287,307 B1 | 9/2001 | Abboudi |
| 6,325,625 B1 | 12/2001 | Meyer |
| 6,355,038 B1 | 3/2002 | Pisharodi |
| 6,440,135 B2 | 8/2002 | Orbay |
| 6,458,131 B1 | 10/2002 | Ray |
| 6,460,700 B2 | 10/2002 | Weisshaupt |
| 6,530,933 B1 | 3/2003 | Yeung |
| 6,572,617 B1 | 6/2003 | Senegas |
| 6,610,091 B1 | 8/2003 | Reiley |
| 6,626,909 B2 | 9/2003 | Chin |
| 6,626,916 B1 | 9/2003 | Yeung |
| 6,626,929 B1 | 9/2003 | Bannerman |
| 6,635,087 B2 | 10/2003 | Angelucci |
| 6,652,527 B2 | 11/2003 | Zucherman |
| 6,660,007 B2 | 12/2003 | Khanna |
| 6,663,654 B1 | 12/2003 | Husain |
| 6,669,697 B1 | 12/2003 | Pisharodi |
| 6,712,820 B2 | 3/2004 | Orbay |
| 6,719,795 B1 | 4/2004 | Cornwall |
| 6,767,351 B2 | 7/2004 | Orbay |
| 6,811,567 B2 | 11/2004 | Reiley |
| 6,880,699 B2 | 4/2005 | Gallagher |
| 6,974,478 B2 | 12/2005 | Reiley |
| 6,981,990 B2 | 1/2006 | Keller |
| 6,997,953 B2 | 2/2006 | Chung |
| 7,074,239 B1 | 7/2006 | Cornwall |
| 7,087,084 B2 | 8/2006 | Reiley |
| 7,090,676 B2 | 8/2006 | Huebner |
| 7,201,751 B2 | 4/2007 | Zucherman |
| 7,264,620 B2 | 9/2007 | Taylor |
| 7,320,689 B2 | 1/2008 | Keller |
| 7,344,537 B1 | 3/2008 | Mueller |
| 7,452,368 B2 | 11/2008 | Liberatore |
| 7,569,067 B2 | 8/2009 | Keller |
| 7,625,376 B2 | 12/2009 | Brumfield |
| 7,744,598 B2 | 6/2010 | Brumfield |
| 2002/0017472 A1 | 2/2002 | Weisshaupt |
| 2002/0029039 A1 | 3/2002 | Zucherman |
| 2002/0046961 A1 | 4/2002 | Levinson |
| 2002/0120335 A1 | 8/2002 | Angelucci |
| 2002/0128682 A1 | 9/2002 | Prestel |
| 2003/0045935 A1 | 3/2003 | Angelucci |
| 2003/0045936 A1 | 3/2003 | Angelucci |
| 2003/0125738 A1 | 7/2003 | Khanna |
| 2004/0030388 A1 | 2/2004 | Null |
| 2004/0102775 A1 | 5/2004 | Huebner |
| 2004/0106927 A1 | 6/2004 | Ruffner |
| 2004/0162558 A1 | 8/2004 | Hegde |
| 2004/0210222 A1 | 10/2004 | Angelucci |
| 2005/0038436 A1 | 2/2005 | Michelson |
| 2005/0085818 A1 | 4/2005 | Huebner |
| 2005/0107877 A1 | 5/2005 | Blain |
| 2005/0119657 A1 | 6/2005 | Goldsmith |
| 2005/0131412 A1 | 6/2005 | Olevsky |
| 2005/0149021 A1 | 7/2005 | Tozzi |
| 2005/0182407 A1 | 8/2005 | Dalton |
| 2005/0234765 A1 | 10/2005 | Blumberg |
| 2005/0251138 A1 | 11/2005 | Boris |
| 2005/0273100 A1 | 12/2005 | Taylor |
| 2006/0064091 A1 | 3/2006 | Ludwig |
| 2006/0079931 A1 | 4/2006 | Brennan |
| 2006/0190033 A1 | 8/2006 | Molloy |
| 2006/0247635 A1 | 11/2006 | Gordon |
| 2007/0123869 A1 | 5/2007 | Chin |
| 2007/0219582 A1 | 9/2007 | Brunelle |
| 2007/0276376 A1 | 11/2007 | Link |
| 2008/0009865 A1 | 1/2008 | Taylor |
| 2008/0183217 A1 | 7/2008 | Glaser |
| 2008/0215096 A1 | 9/2008 | Nash |
| 2008/0302688 A1 | 12/2008 | Iaconi-Forrer |
| 2010/0016900 A1 | 1/2010 | Terres |
| 2010/0057127 A1 | 3/2010 | McGuire |
| 2011/0106083 A1 | 5/2011 | Voellmicke |
| 2011/0106084 A1 | 5/2011 | Gamache |
| 2011/0106087 A1 | 5/2011 | Gamache |
| 2011/0106169 A1 | 5/2011 | Zalenski |

FOREIGN PATENT DOCUMENTS

| | | |
|---|---|---|
| WO | WO 9605778 | 2/1996 |
| WO | WO 9709940 | 3/1997 |
| WO | WO 9937221 | 7/1999 |
| WO | WO 0044290 | 8/2000 |
| WO | WO 03007826 | 1/2003 |
| WO | WO 03020142 | 3/2003 |
| WO | WO 03101319 A3 | 1/2004 |
| WO | WO 2005041752 A2 | 5/2005 |
| WO | WO 2005096969 | 10/2005 |
| WO | WO 2005041752 A3 | 5/2006 |
| WO | WO 2006104487 | 10/2006 |
| WO | WO 2007127918 | 11/2007 |
| WO | WO 2011040983 | 4/2011 |

OTHER PUBLICATIONS

Stanescue, "Morphometic Evaluation of the Cervico-Thoracic Junction, Practical Considerations for Posterior Fixation of the Spine", Spine, vol. 19, No. 18, 1994, pp. 2082-2088, J.B. Lippincott Co.

* cited by examiner

BONE GRAFT LOADING INSTRUMENTS AND METHODS OF CONNECTING A BONE GRAFT TO A BONE PLATE

BACKGROUND

In many spinal and orthopedic procedures bone graft is used in connection with a plate or other instrument to facilitate fusion of bone. In laminoplasty procedures, for example, in which the lamina of a vertebra is cut and spaced apart to expand the spinal canal, a bone graft is frequently inserted into the expanded space. The bone graft is typically connected to a plate, which assists in holding the bone graft in place during the fusion process and stabilizes the vertebra until fusion is complete. Connecting the bone graft to the plate can be challenging as the plate and the bone graft are small and difficult to handle. For this reason, there is a need for improved instruments and techniques for connecting bone graft to a plate or other implant.

SUMMARY

Disclosed herein are instruments and methods for connecting one of a plurality of bone grafts to one of a plurality of bone plates. The instruments and methods disclosed herein are particularly suited for use in connection with laminoplasty systems having a plurality of bone grafts of differing lengths and a plurality of laminoplasty plates of differing lengths.

In one aspect, a laminoplasty system may include a set of bone grafts, a set of bone plates, and an instrument for connecting the bone grafts to one of the bone plates. The bone grafts of the set of bone grafts may each have a graft length and a plurality of the bone grafts of the set of bone grafts may have differing graft lengths. A plurality of the bone plates of the set of bone plates may include a first plate segment, a second plate segment, and a central plate segment interposed between the first plate segment and the second plate segment. The first plate segment may include a first hole for receiving a bone anchor, the second plate segment may include a second hole for receiving a bone anchor, and the central plate segment may include a graft opening for receiving an anchor to connect one of the bone grafts. The first hole of the first bone plate may be spaced apart from the second hole by a plate length and at least some of the plurality of bone plates may have differing plate lengths. The instrument may include an instrument body having a plurality of spaced apart graft chambers. A first one of the graft chambers may have a first end, a second end, and a chamber length extending between the first end and the second end, the chamber length corresponding to at least one of the graft lengths. The instrument body may include a first protrusion proximate the first end of the first graft chamber and a second protrusion proximate the second end of the first graft chamber. The first protrusion may be sized to fit within the first hole of a first one of the bone plates and the second protrusion may be sized to fit within the second hole of the first bone plate. The first protrusion may be spaced apart from the second protrusion a first protrusion distance corresponding to the plate length of the first bone plate.

In another aspect, an instrument for positioning one of a plurality of bone grafts relative to one of a plurality of bone plates includes an instrument body having a plurality of spaced apart graft chambers. A first one of the graft chambers having a first end, a second end, and a chamber length extending between the first end and the second end. The first end of the first graft chamber may include a first chamber surface for receiving a first plate segment of a first one of the plurality of the bone plates and the second end of the first graft chamber may include a second chamber surface for receiving a second plate segment of the first plate. The first graft chamber may include a central chamber surface interposed between the first chamber surface and the second chamber surface for receiving a first one of the bone grafts. The central chamber surface may have a first chamber length corresponding to a graft length of a first one of the bone grafts.

In another aspect, a method of positioning a bone graft relative to a bone plate includes selecting a bone graft from a set of bone grafts of differing bone graft lengths, selecting a graft chamber from a plurality of graft chambers of an instrument for positioning a bone graft relative to a bone plate based on the graft length of the selected bone graft, positioning the selected bone graft in the selected graft chamber, positioning a bone plate over the selected bone graft in the selected graft chamber, connecting the bone plate to the selected bone graft.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the devices and methods disclosed herein and, although not to scale, show relative dimensions.

DETAIL DESCRIPTION OF EXEMPLARY EMBODIMENTS

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

Figure 1:
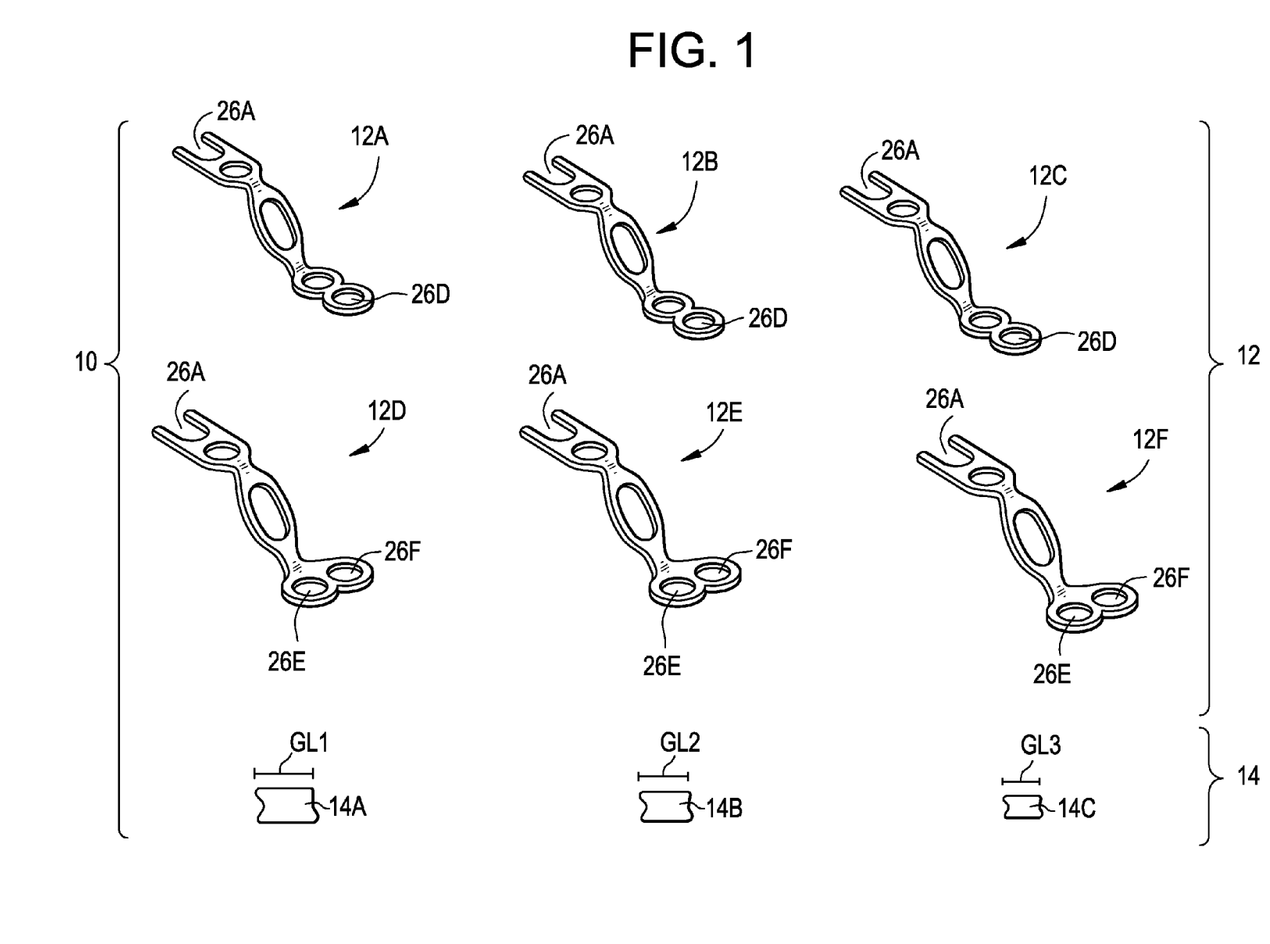
FIG. 1 is an exemplary embodiment of a laminoplasty system including a set of bone plates and a set of bone grafts.
Figure 4:
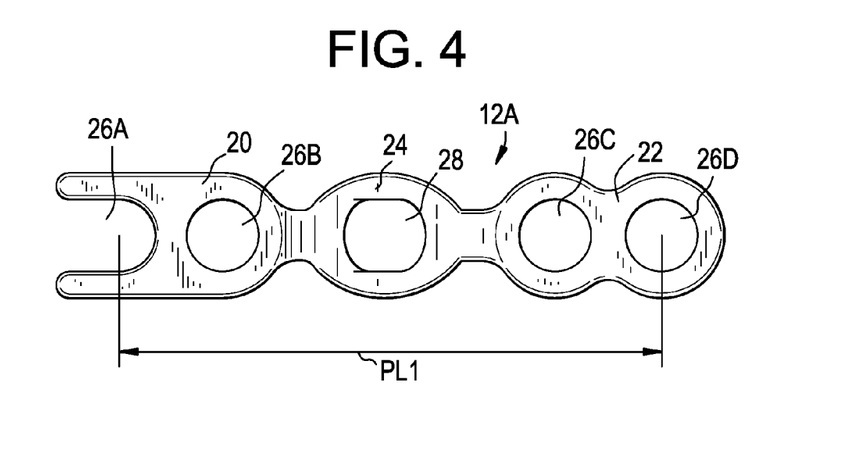
FIG. 4 is a perspective view of the bone plate of FIG. 2.
Figure 5:
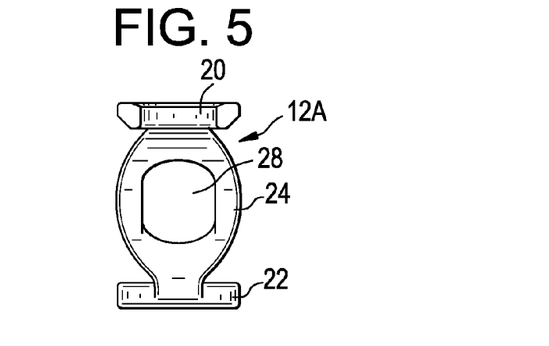
FIG. 5 is a front view of the bone plate of FIG. 2.

FIG. 1 illustrates an exemplary laminoplasty system 10 including a set of bone plates 12 and a set of bone grafts 14. The exemplary bone plates 12 and the exemplary bone grafts 14 are particularly suited for use in a surgical procedure to alleviate spinal cord compression by expanding the spinal canal, typically by displacing bone, such as the lamina, that surrounds the spinal cord. This procedure, generally referred to as laminoplasty, typically involves making two types of cuts into the lamina, a complete osteotomy through the lamina on one side of the spine and a partial osteotomy, or "green stick", on the contra-lateral lamina, which preserves the bottom cortex and creates a flexible hinge in the bone. This bridge of lamina bone is then levered open about the hinge and fixed with one of the bone grafts 14, one of the plates 12, and a plurality of screws. Exemplary laminoplasty plates, bone grafts, and methods of expanding the spinal canal of a vertebra are described in commonly owned, co-pending US Patent Application Publication No. US 2011/0106083, entitled "Laminoplasty Plates and Methods of Expanding the Spinal Canal" concurrently filed herewith, which is incorporated herein by reference. Typically, the bone graft 14 is connected to the bone plate 12 prior to connecting the plate 12 to the vertebra, as illustrated in FIG. 4. The exemplary laminoplasty system also includes an instrument 16 for connecting one or more of the bone grafts 14 to one or more of the bone plates 12, as illustrated in FIGS. 7-10.

The set of bone grafts 14 may include any number of bone grafts of varying sizes and shapes and, in particular, may include plurality of bone grafts of differing lengths. For example, a set of bone grafts may include a first bone graft 14A having a first bone graft length GL1, a second bone graft 14B having a second bone graft length GL2, and a third bone graft 14C having a third bone graft length GL3, as illustrated in FIG. 1. The first bone graft length GL1, the second bone graft length GL2, and the third bone graft length GL3 may distinct from each other. For example, the first bone graft length GL1 may be greater than the second bone graft length GL2 and the second bone graft length GL2 may be greater than the third bone graft length GL3. During the surgical procedure, the surgeon may select an appropriate length bone graft 14 based on the length of the space between bone segments into which the bone graft 14 is to be placed. The bone grafts may be constructed from cortical or cancellous bone, or composites thereof, and may be allograft or autograft. In one exemplary laminoplasty system, a set of bone grafts for laminoplasty includes bone grafts of the following distinct graft lengths: 4 mm, 6 mm, 8 mm, 10 mm, 12 mm, 14 mm, 16 mm, and 18 mm.

The set of bone plates 14 may include a plurality of bone plates of varying sizes and shapes. For example, a set of bone plates 14 may include a plurality of bone plates of two types: in-line bone plates 12A-C and offset bone plates 12D-F, as illustrated in FIG. 1. The exemplary in-line plates 12A-C include a plurality of bone screw receiving holes aligned along the central longitudinal axis of the bone plate. The exemplary off-set plates 12D-F include a plurality of bone screw receiving holes, at least two of which are off-set from the central longitudinal axis of the bone plate. The exemplary in-line bone plates 12A-C and offset bone plates 12D-F may come in differing lengths in the system 10. During the surgical procedure, the surgeon may select an appropriate length bone plate based on the length of the space between bone segments the bone plate is to connect. The bone plates 12 may be constructed of any biocompatible material suitable for implantation within the human body, including, for example, stainless steel, titanium and titanium alloys, and polymers, including biodegradable polymers. In one exemplary laminoplasty system, the inline bone plates and the offset bone plates are provided in the following differing lengths: 6 mm, 8 mm, 10 mm, 12 mm, 14 mm, 16 mm, and 18 mm.

Figure 2:
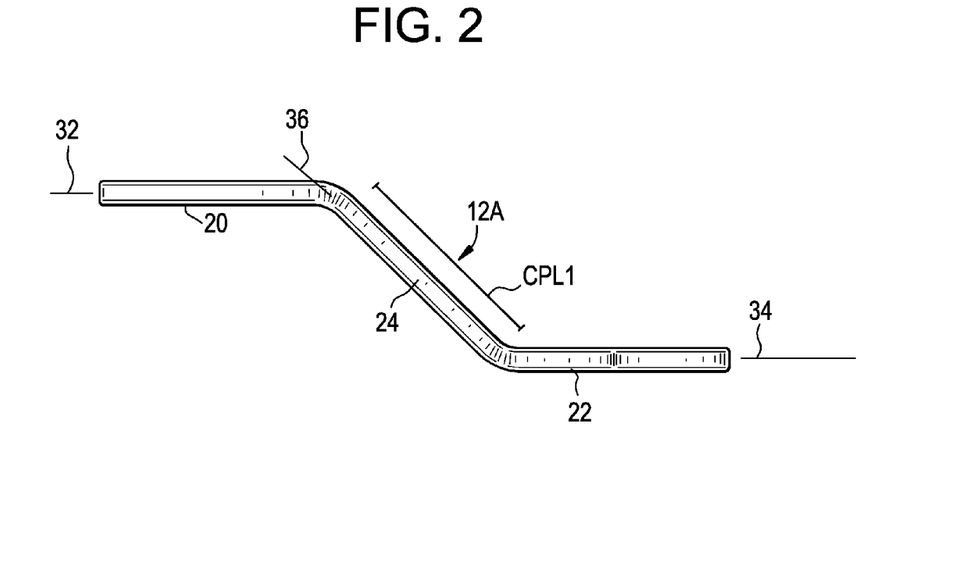
FIG. 2 is a side view of a bone plate of the laminoplasty system of FIG. 1.
Figure 3:
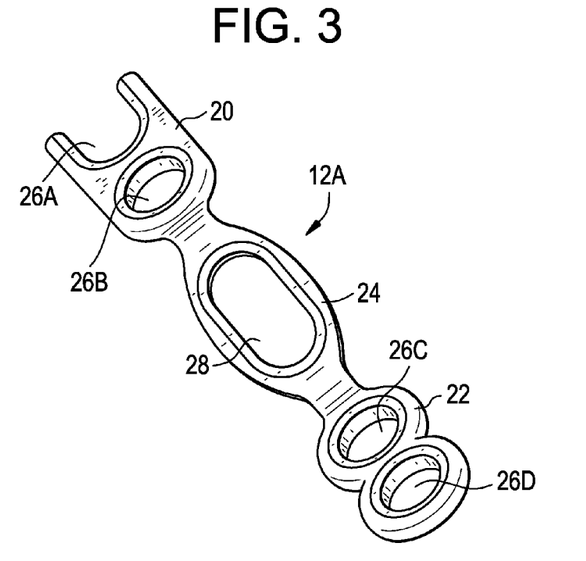
FIG. 3 is a top view of the bone plate of FIG. 2.

Referring to FIGS. 2-6, the exemplary bone plates 12, including bone plates 12A-12D, may include a first plate segment for connecting to a first bone segment, such as the lamina of a vertebra, a second plate segment for connecting to a second bone segment, such as the lateral mass of the vertebra, and a central plate segment for holding a bone graft positioned between the first and second bone segments if a bone graft is employed. Referring to FIGS. 2-4, for example, exemplary in-line bone plate 12A includes a first plate segment 20, a second plate segment 22, and a central plate segment 24 interposed between the first plate segment 20 and the second plate segment 22. The first plate segment 20 may include one or more bone anchor receiving holes. In the exemplary embodiment, for example, the first plate segment 20 includes a first bone anchor receiving hole 26A in the form of an open ended slot and an enclosed, generally circular second bone anchor receiving hole 26B. The second plate segment 22 may include one or more bone anchor receiving holes. In the exemplary embodiment, for example, the second plate segment 22 includes a third bone anchor receiving hole 26C and a fourth bone anchor receiving hole 26D. In the in-line bone plates 12A-C, the first, second, third and fourth bone anchor receiving holes 26A-D are aligned along the central longitudinal axis of the bone plate. The central plate segment 24 may include one or more graft openings for receiving an anchor 30 to connect to one of the bone grafts 14. In the exemplary bone plate 12A, for example, the central plate segment 24 includes an elongated, closed slot 28.

Figure 6:
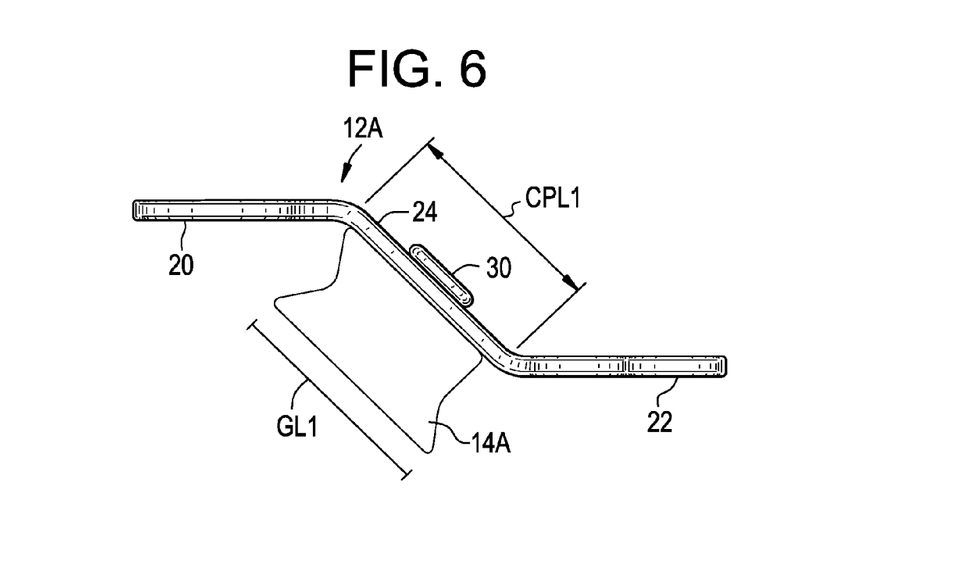
FIG. 6 is a side view of a bone plate and a bone graft of the laminoplasty of FIG. 1, illustrating the bone graft connected to the bone plate.

The exemplary bone plates of the system 10 may include a plate length generally extending between the furthest spaced apart bone anchor receiving holes provided on the bone plate. The exemplary bone plate 12A, for example, has a first plate length PL1 generally extending between the first bone anchor receiving hole 26A and the fourth bone anchor receiving hole 26D. Bone plate 12B and bone plate 12C may have distinct plate lengths from bone plate 12A and from each other. Likewise, bone plates 12D-F may have distinct plate lengths. The central plate segment 24 of the exemplary bone plates of the system 10 may have a central plate segment length that is greater than or approximately equal to the graft length of a bone graft 14 of the system 10. Referring to FIGS. 2 and 6, for example, the bone plate 12A may have a central plate segment length CPL1 that is approximately equal to the graft length GL1 of bone graft 14A.

The bone plates 12 of the exemplary system 10 may have a geometry to facilitate connection to the lamina of a vertebra at one end, e.g., at the first plate segment, and connection to the lateral mass of the vertebra at the other end, e.g. at the second plate segment. Referring to FIG. 2, for example, the first plate segment 20 and the second plate segment 22 of the exemplary bone plate 12 lie in separate, approximately parallel planes, e.g., first plane 32 and second plane 34, respectively, and the central plate segment 24 connects the first plate segment 20 and the second plate segment 22 and lies in a plane, e.g., third plane 36 that intersects the parallel planes.

The off-set plates 12D-12F of the system 10 may have configuration analogous to that of the in-line plates 12A-12C except the second segment of the off-set plates includes two off-set bone anchor receiving holes 26E, 26F that are positioned off-set from the central longitudinal axis of the bone plate.

Referring to FIGS. 7-10, an exemplary instrument 16 for connecting the bone grafts 14 of the system 10 to one of the bone plates 12 may include an instrument body 40 having a plurality of spaced apart graft chambers 42, each of which is configured to receive one the bone grafts 14 and one of the bone plates 12 to connect to the bone graft 14. The instrument body 40 in the exemplary embodiment is in the shape of a generally rectangular block into which the graft chambers 42 are formed. The instrument body 40 may have other shapes and may be constructed of any material suitable for use as a medical or surgical instrument, including, for example, stainless steel. The exemplary instrument 16 includes a side-by-side array of graft chambers 42A-42G provided within the instrument body 40. Each graft chamber 42A-42G is open at the top surface 44 of the instrument body 42 to permit bone grafts 14 and bone grafts 12 to be positioned within the graft chambers 42A-G. Any number of graft chambers 42 may be provided, including a single graft chamber. In the exemplary instrument 16, seven graft chambers 42A-G of distinct size are provided corresponding to the seven distinct lengths of bone plate provided in an exemplary system. In the exemplary instrument 16, the graft chambers are arranged by size, from smallest 42A to largest 42G, in a side-by-side array. In the exemplary instrument, each graft chamber 42A-G is sized to receive two lengths of bone graft and to receive one length of bone plate, although other sizing schemes are possible, including for example, one graft length and one plate length per graft chamber, depending on the configuration of the system. Indicia indicating the bone plate length (e.g., "PLATE SIZE") and bone graft length (e.g., "GRAFT SIZE") of each of the graft chambers may be provided proximate each graft chamber on the top surface 44 of the instrument 16.

The graft chambers may have a size and shape corresponding to the size and shape of the bone plates 12 and bone grafts 14 provided in the associated system 10. The graft chambers 42 each may have an analogous, uniform shape, albeit with varying sizes, as in the exemplary instrument 40 or may have non-uniform shapes, depending on the shapes of the bone plates 12 provided in the associated system 10.

In the exemplary instrument 16, a first one of the graft chambers 42A has a first end 50A, a second end 52A, and a chamber length CL1 extending between the first end 50A and the second end 52A. The exemplary instrument 16 includes a first protrusion 54A, in the form of a cylindrical post, proximate the first end 50A of the first graft chamber 42A and a second protrusion 54B, in the form of a cylindrical post, proximate the second end 52A of the first graft chamber 42A. The first protrusion 54A is sized to fit within a hole of one of the bone plates 12, for example, the first hole 26A the first bone plate 12A, and the second protrusion 54B may be sized to fit within a second hole of the bone plate, for example, the fourth hole 26D of the first bone plate 12A. The diameter of the first protrusion 54A and the diameter of the second protrusion 56A may approximate the diameter of the first hole 26A and the diameter of the fourth hole 26D, respectively, to thereby stabilize and minimize motion of the first bone plate 12A relative to the instrument 16 when the plate is connected to a bone graft. The first protrusion 54A may be spaced apart from the second protrusion 54B a first protrusion distance PD1 corresponding to the plate length of the bone plate. For example, the first protrusion distance PD1 may be approximately equal to the first plate length PL1 of the in-line first bone plate 12A, e.g. the distance between the first hole 26A and the fourth hole 26D.

The graft chambers may be configured to receive bone plates having differing bone anchor receiving hole configurations. For example, the first graft chamber 42A may be configured to receive one of the off-set plates 12D-F in addition to the in-line plates 12A-C. The first graft chamber 42A may include a third protrusion 58A and a fourth protrusion 60A, both in the form of a cylindrical post, may be arranged to fit within the off-set bone anchor receiving holes 26E, 26F provided on the second plate segment of one of the offset plates. The third protrusion 58A and the fourth protrusion 60A are spaced are from the first protrusion 54A a protrusion distance equal to the plate length of the respective offset plate, i.e., the distance between the first bone anchor hole 26A on the first plate segment and the two offset bone anchor holes 26E, 26F.

The first end 50A of the first graft chamber 42A includes a first chamber surface 62A for receiving the first plate segment 20 of the first bone plate 12A and the second end 52A of the first graft chamber 42A includes a second chamber surface 64A for receiving the second plate segment 22 of the first plate 12A. The first graft chamber 42A includes central chamber surface 66A interposed between the first chamber surface 62A and the second chamber surface 64A. The first chamber surface 62A, the second chamber surface 64A, and the central chamber surface 66A may be oriented in a manner analogous to the relative orientation of the first plate segment 20, the second plate segment 22, and the central plate segment 24. For example, the first chamber surface 62A of the first graft chamber 42A may be planar and may define a first plane. The second chamber surface 64A of the first graft chamber also may be planar and may define a second plane approximately parallel to the first plane. The central chamber surface 66A of the first graft chamber also may be planar and may define a third plane that intersects the first plane and the second plane. A bone graft, when positioned in the graft chamber 42A, rests against the central chamber surface 66A. The length of central chamber surface 66A, between the intersection with the first chamber surface 62A and the intersection with the second chamber surface 64A, defines a first chamber length CL1 of the first graft chamber 42A. The first chamber length CL1 corresponds to the length of the central plate segment 24 of the first bone plate 12A. For example, the first chamber length CL1 is approximately equal to the central plate segment length CPL1. In addition, the first chamber length CL1 is greater than or equal to the lengths of the two grafts that the graft chamber 42A is sized for. For example, the first chamber length CL1 may be greater than the graft length GL1 of a first bone graft 14A (e.g., greater than 4 mm) and the first chamber length CL1 may be approximately equal to the graft length of a second bone graft (e.g., equal to 6 mm).

The additional graft chambers 42B-42G may be configured in a manner analogous to the first graft chamber. For example, a second graft chamber 42B may include a first protrusion 54B spaced apart from a second protrusion 56B a second protrusion distance PD2 that is approximately equal to the plate length of a second one of the bone plates. The second protrusion distance PD2 is distinct (i.e., greater than) the first protrusion distance PD1 as the second bone plate has a plate length distinct (i.e., greater than) the first plate length PL1. The second graft chamber 42B also may have a first chamber surface 62B, a second chamber surface 64B, and central chamber surface 66B interposed between the first chamber surface 62B and the second chamber surface 64B. The central chamber surface 66B may have a second chamber length CL2, between the intersection with the first chamber surface 62B and the intersection with the second chamber surface 64B, corresponding to the length of the central plate segment of the second one of the bone plates. For example, the second chamber length CL2 may be approximately equal to the central plate segment length of the second bone plate. In addition, the second chamber length CL2 may be distinct from (e.g., greater than) the first chamber length CL1, as the central plate segment length of the second plate may be distinct from (e.g., greater than) the central plate segment length of the first bone plate. In addition, the second chamber length CL2 may be greater than or equal to the lengths of the two grafts that the graft chamber 42B is sized for. For example, the second chamber length CL2 may be greater than the graft length of the second bone graft (e.g., greater than 6 mm) and the second chamber length CL2 may be approximately equal to the graft length of a third bone graft (e.g., equal to 8 mm).

The first chamber surface 62B, the second chamber surface 64B, and the central chamber surface 66B of the second graft chamber 42B may be oriented in a manner analogous to the relative orientation of the first plate segment, the second plate segment, and the central plate segment of the second bone plate. For example, the first chamber surface 62B of the second graft chamber 42B may be planar and may define a fourth plane. The second chamber surface 64B of the second graft chamber 42B also may be planar and may define a fifth plane approximately parallel to the fourth plane. The central chamber surface 66B of the second graft chamber 42B also may be planar and may define a sixth plane that intersects the fourth plane and the fifth plane. The first plane (first chamber surface 62A) and the fourth plane (first chamber surface 62B) are parallel, the second plane (second chamber surface 64A) and the fifth plane (second chamber surface 64B) are co-planar, and the third plane (central chamber surface 66A) and the sixth plane (central chamber surface 66A) are co-planar.

Figure 7:
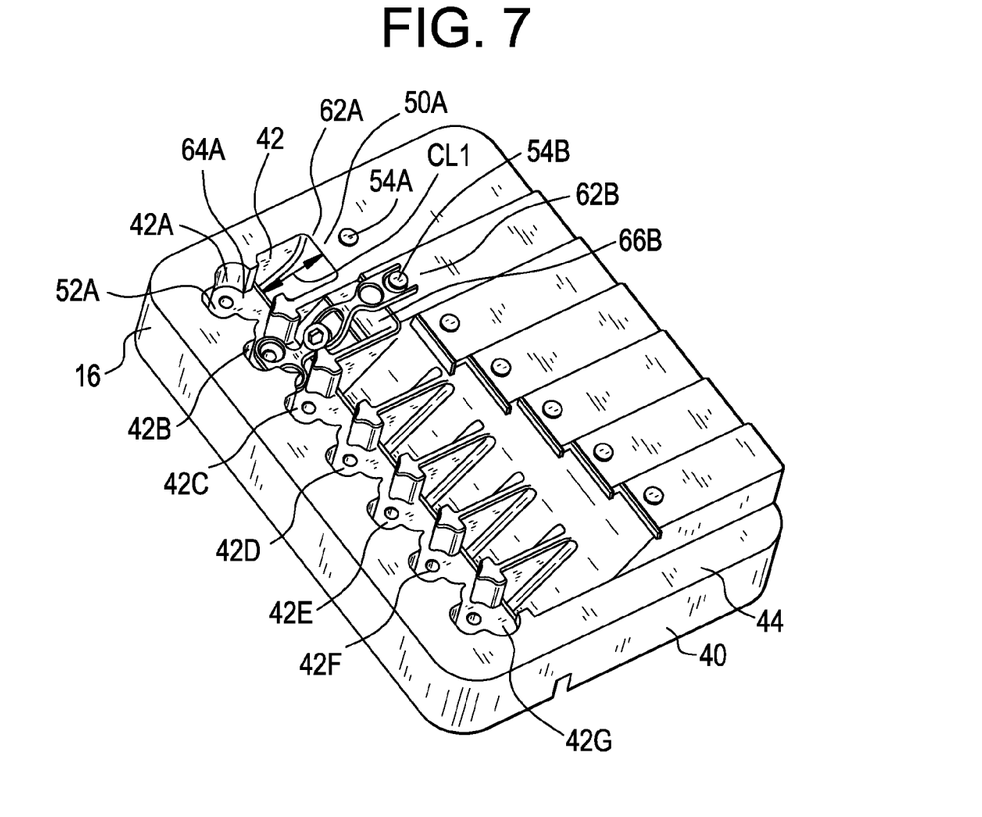
FIG. 7 is a perspective view of an exemplary embodiment of an instrument for connecting a bone graft to a bone plate.

An exemplary method of positioning a bone graft relative to a bone plate using the exemplary instrument 16 includes selecting a bone graft from a set of bone grafts provided in a system of bone grafts and bone plates of differing lengths. In a laminoplasty procedure, one or more trials of differing sizes may be positioned in the space created between bone segments of the vertebrae, e.g., the space between the lamina and the lateral mass of the vertebra, to measure the space after expansion of the spinal canal. The bone graft is selected based on the size of the space as measured by the trial. A bone plate may also be selected from a set of bone plates provided in the system based on the size of the space measured by the trail. For example, if the space is measured by a trial to be 8 mm, a bone graft having a graft length GL of 8 mm may be selected and a plate having a central plate segment length CPL of 8 mm may be selected.

Figure 8:
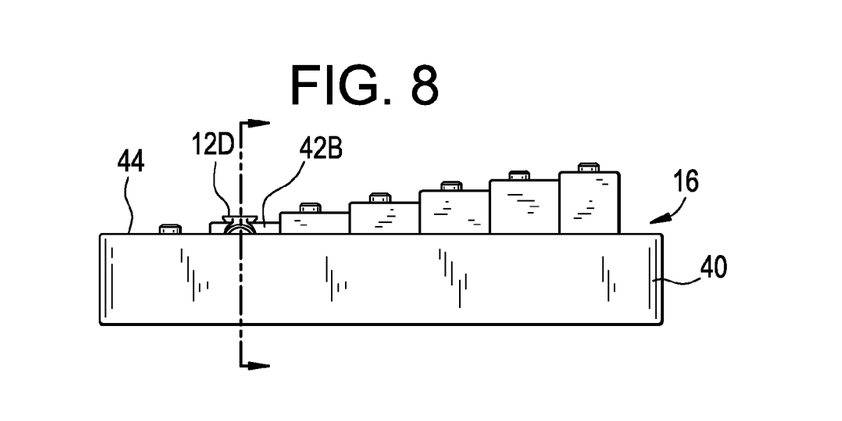
FIG. 8 is a side view of the instrument of FIG. 7.
Figure 9:
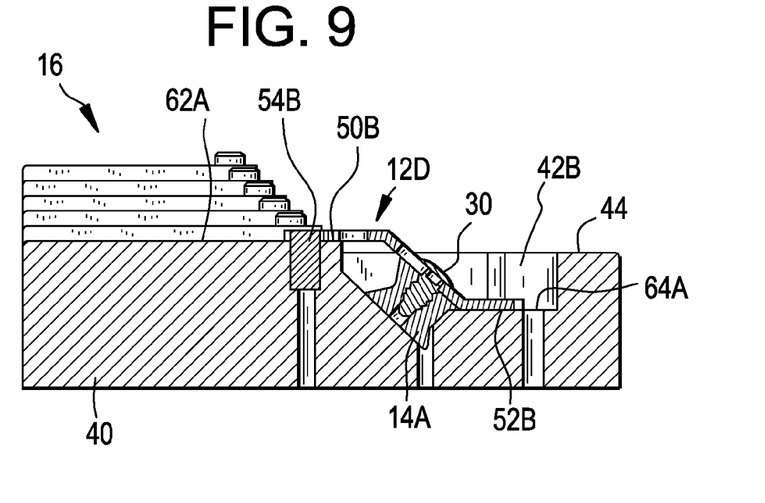
FIG. 9 is a side view in cross section of the instrument of FIG. 7.
Figure 10:
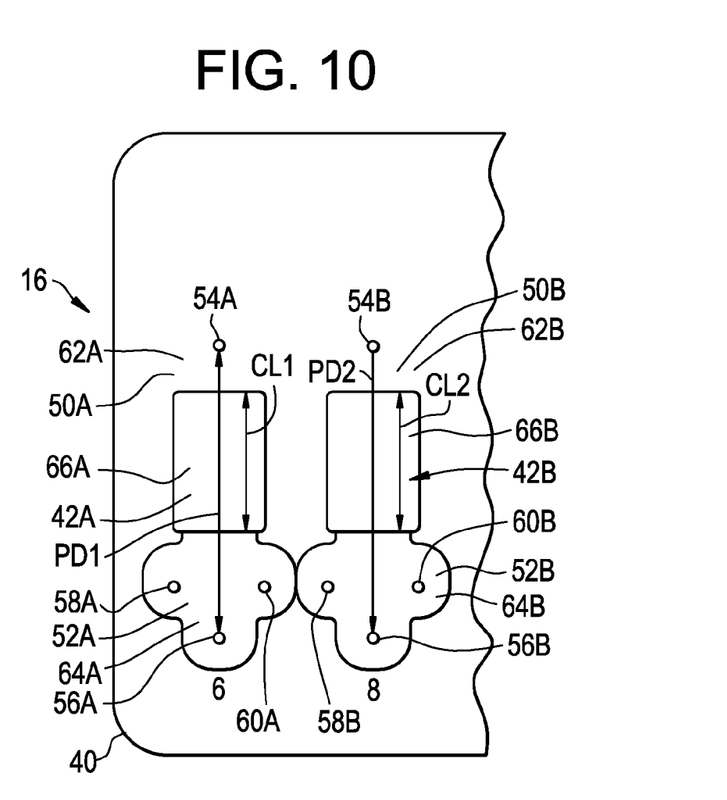
FIG. 10 is a partial top view of the instrument of FIG. 7, illustrating a first graft chamber of the instrument.

A graft chamber 42 may be selected from the plurality of graft chambers 42A-42G of the instrument 16 based on the graft length GL of the selected bone graft and the central plate segment length CPL of the selected bone plate. For example, graft chamber 42B may be selected based on the selected graft having a graft length of 8 mm (or 6 mm) and the selected plate having a central plate segment length CPL of 8 mm. The selected bone graft may be positioned in the selected graft chamber with the graft resting against the central chamber surface 66 of the selected graft chamber. The selected bone plate may then be positioned over the selected bone graft within the graft chamber. For example, if the bone graft is positioned in graft chamber 42B and one of the in-line bone plates 12A-12C is selected, e.g., first bone plate 12A, the first hole 26A of the first bone plate 12A is positioned over first protrusion 54B and the fourth hole 26D of the first bone plate 12A is positioned over second protrusion 56B. Alternatively, if one of the off-set bone plates 12D-F is selected, the first hole of the off-set plate is positioned over first protrusion 54B and the two off-set holes 26E, 26F are positioned over the third and fourth protrusions 58B, 60B, respectively. The selected bone plate may then be connected to the selected bone graft by positioning an anchor, e.g., anchor 30, through an opening, e.g., slot 28, in the bone plate and into the bone graft. FIGS. 7-9 illustrate an off-set plate 12D having a central plate segment length CPL of 8 mm connected to a bone graft 14A having a graft length of 6 mm positioned in the graft chamber 42B.

Once the bone graft is connected to the bone plate, the bone plate and bone graft may be removed from the instrument and connected to the expanded vertebra. The plate and bone graft may be manipulated by hand by the surgeon or may be manipulated by an instrument, such as, for example, a forceps, plate holder, or the like. An exemplary plate holder is described in commonly owned, co-pending US Patent Application Publication No. US 2011/0106084, entitled "Bone Plate Holder" concurrently filed herewith, which is incorporated herein by reference.

In the exemplary instrument 16, the graft chambers 42A-42G have the following sizes:

TABLE 1

| Graft Chamber | Chamber Length (CL) | Graft Length (GL) | Plate Size |
| --- | --- | --- | --- |
| 42A | 6 mm | 4/6 mm | 6 mm |
| 42B | 8 mm | 6/8 mm | 8 mm |
| 42C | 10 mm | 8/10 mm | 10 mm |
| 42D | 12 mm | 10/12 mm | 12 mm |
| 42E | 14 mm | 12/14 mm | 14 mm |
| 42F | 16 mm | 14/16 mm | 16 mm |
| 42G | 18 mm | 16/18 mm | 18 mm |

Wherein, chamber length (CL) refers to the length of central chamber surface (66) of each graft chamber, graft length refers to the two graft lengths (GL) accommodated by each graft chamber, and plate size refers to the central plate segment length (CPL) accommodated by each graft chamber.

While the devices and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:
1. A laminoplasty system comprising:
a set of bone grafts, the bone grafts of the set each having a graft length, a plurality of the bone grafts of the set of bone grafts having differing graft lengths,
a set of bone plates, a plurality of the bone plates of the set of bone plates including a first plate segment, a second plate segment, and a central plate segment interposed between the first plate segment and the second plate segment, the first plate segment including a first hole for receiving a bone anchor, the second plate segment including a second hole for receiving a bone anchor, the central plate segment including a graft opening for receiving an anchor to connect one of the bone grafts, the first hole spaced apart from the second hole by a plate length, at least some of the plurality of bone plates having differing plate lengths, and an instrument for connecting the bone grafts to one of the bone plates, the instrument including an instrument body having a plurality of spaced apart graft chambers, a first one of the graft chambers having a first end, a second end, and a chamber length extending between the first end and the second end, the instrument body including a first protrusion proximate the first end of the first graft chamber and a second protrusion proximate the second end of the first graft chamber, the first protrusion being sized to fit within the first hole of a first one of the bone plates, the second protrusion being sized to fit within the second hole of the first bone plate, the first protrusion spaced apart from the second protrusion a first protrusion distance corresponding to the plate length of the first bone plate.

2. The laminoplasty system of claim 1, wherein the first protrusion distance is approximately equal to the plate length of the first bone plate.

3. The laminoplasty system of claim 1, wherein the instrument body includes a third protrusion proximate a first end of a second one of the graft chambers and a fourth protrusion proximate a second end of the second graft chamber, the third protrusion being sized to fit within the first hole of a second one of the bone plates, the fourth protrusion being sized to fit within the second hole of the second bone plate, the second bone plate having a second plate length distinct from the first plate length, the third protrusion being spaced apart from the fourth protrusion a second protrusion distance, distinct from the first protrusion distance, approximately equal to the plate length of the second bone plate.

4. The laminoplasty system of claim 3, wherein the first chamber has a first chamber length approximately equal to a length of the central plate segment of the first bone plate and greater than a first graft length of a first one of the plurality of bone grafts.

5. The laminoplasty system of claim 4, wherein the second chamber has a second chamber length approximately equal to a length of the central segment of a second one of the plurality of bone plates and greater than a second graft length of a second one of the plurality of bone grafts, the second chamber length being distinct from the first chamber length.

6. The laminoplasty system of claim 5, wherein the instrument body includes first indicia proximate the first graft chamber indicating the first graft length and the plate length of the first plate and second indicia proximate the second graft chamber indicating the second graft length and the plate length of the second plate.

7. The laminoplasty system of claim 1, wherein the first end of the first graft chamber includes a first chamber surface for receiving the first plate segment of the first plate, the second end of the first graft chamber includes a second chamber surface for receiving the second plate segment of the first plate, and the first graft chamber includes central chamber surface interposed between the first chamber surface and the second chamber surface for receiving a first one of the bone grafts, the central chamber surface having a first chamber length.

8. The laminoplasty system of claim 7, wherein a second one of the graft chambers includes a first chamber surface for receiving the first plate segment of a second one of the plates, a second chamber surface for receiving the second plate segment of the second plate, and a central chamber surface interposed between the first chamber surface and the second chamber surface for receiving a second one of the bone grafts, the central chamber surface of the second graft chamber having a second chamber length.

9. The laminoplasty system of claim 8, wherein the second chamber length is distinct from the first chamber length.

10. The laminoplasty system of claim 8, wherein the first chamber surface of the first graft chamber is planar and defines a first plane, the second chamber surface of the first graft chamber is planar and defines a second plane approximately parallel to the first plane, and the central chamber surface of the first graft chamber is planar and defines a third plane that intersects the first plane and the second plane.

11. The laminoplasty system of claim 10, wherein the first chamber surface of the second graft chamber is planar and defines a fourth plane, the second chamber surface of the second graft chamber is planar and defines a fifth plane approximately parallel to the third plane, and the central chamber surface of the second graft chamber is planar and defines a sixth plane that intersects the fourth plane and the fifth plane.

12. The laminoplasty system of claim 11, wherein the first plane and the fourth plane are parallel, the second plane and the fifth plane are co-planar, and the third plane and the sixth plane are co-planar.

13. An instrument for positioning one of a plurality of bone grafts relative to one of a plurality of bone plates, the instrument comprising:
  an instrument body having a plurality of spaced apart graft chambers, a first one of the graft chambers having a first end, a second end, and a chamber length extending between the first end and the second end, the first end of the first graft chamber including a first chamber surface for receiving a first plate segment of a first one of the plurality of the bone plates, the second end of the first graft chamber including a second chamber surface for receiving a second plate segment of the first plate, the first graft chamber including a central chamber surface interposed between the first chamber surface and the second chamber surface for receiving a first one of the bone grafts, the central chamber surface having a first chamber length corresponding to a graft length of a first one of the bone grafts,
  wherein a second one of the graft chambers includes a first chamber surface for receiving a first plate segment of a second one of the bone plates, a second chamber surface for receiving a second plate segment of the second plate, and a central chamber surface interposed between the first chamber surface and the second chamber surface for receiving a second one of the bone grafts, the central chamber surface of the second graft chamber having a second chamber length,
  wherein the first chamber surface of the first graft chamber is planar and defines a first plane, the second chamber surface of the first graft chamber is planar and defines a second plane approximately parallel to the first plane, and the central chamber surface of the first graft chamber is planar and defines a third plane that intersects the first plane and the second plane.

14. The instrument of claim 13, wherein the second chamber length is distinct from the first chamber length.

15. The instrument of claim 13, wherein the first chamber surface of the second graft chamber is planar and defines a fourth plane, the second chamber surface of the second graft chamber is planar and defines a fifth plane approximately parallel to the third plane, and the central chamber surface of the second graft chamber is planar and defines a sixth plane that intersects the fourth plane and the fifth plane.

16. The instrument of claim 15, the first plane and the fourth plane are parallel, the second plane and the fifth plane are co-planar, and the third plane and the sixth plane are co-planar.

17. A method of positioning a bone graft relative to a bone plate, the method comprising:
    selecting a bone graft from a set of bone grafts of differing bone graft lengths,
    selecting a graft chamber from a plurality of graft chambers of an instrument for positioning a bone graft relative to a bone plate based on the graft length of the selected bone graft,
    positioning the selected bone graft in the selected graft chamber,
    positioning a bone plate over the selected bone graft in the selected graft chamber,
    connecting the bone plate to the selected bone graft.

18. The method of claim 17, wherein the selecting the bone graft includes positioning one or more trials in a space between bone segments and wherein the bone graft is selected based on the size of the space as determined by the trial positioned in the space.

19. The method of claim 18, wherein the bone plate is selected from a set of bone plates having differing plate lengths and wherein the bone plate is selected based on the size of the space as determined by the trial positioned in the space.

20. The method of claim 17, wherein connecting the bone plate to the bone graft includes positioning an anchor through an opening in the bone plate and into the bone graft.

21. The method of claim 20, wherein the opening is an elongated slot.

22. A laminoplasty system comprising:
    a set of bone grafts, the bone grafts of the set each having a graft length, a plurality of the bone grafts of the set of bone grafts having differing graft lengths,
    a set of bone plates, a plurality of the bone plates of the set of bone plates including a first plate segment, a second plate segment, and a central plate segment interposed between the first plate segment and the second plate segment, the first plate segment including a first hole for receiving a bone anchor, the second plate segment including a second hole for receiving a bone anchor, the central plate segment including a graft opening for receiving an anchor to connect one of the bone grafts, the first hole spaced apart from the second hole by a plate length, at least some of the plurality of bone plates having differing plate lengths, and
    an instrument for connecting the bone grafts to one of the bone plates, the instrument including an instrument body having a plurality of spaced apart graft chambers, a first one of the graft chambers having a first end, a second end, and a chamber length extending between the first end and the second end, the first end of the first graft chamber including a first chamber surface for receiving the first plate segment of a first one of the plurality of bone plates, the second end of the first graft chamber including a second chamber surface for receiving the second plate segment of the first bone plate, the first graft chamber including a central chamber surface interposed between the first chamber surface and the second chamber surface for receiving a first one of the bone grafts, the central chamber surface having a first chamber length corresponding to a graft length of the first bone graft.

* * * * *

UNITED STATES PATENT AND TRADEMARK OFFICE
CERTIFICATE OF CORRECTION

| | | |
|---|---|---|
| PATENT NO. | : 8,425,515 B2 | Page 1 of 1 |
| APPLICATION NO. | : 12/609260 | |
| DATED | : April 23, 2013 | |
| INVENTOR(S) | : Gamache et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 604 days.

Signed and Sealed this
Sixteenth Day of December, 2014

Michelle K. Lee
*Deputy Director of the United States Patent and Trademark Office*